United States Patent
Sioshansi et al.

(10) Patent No.: US 8,027,712 B2
(45) Date of Patent: Sep. 27, 2011

(54) ELONGATED MARKERS FOR SOFT TISSUE VOLUME IDENTIFICATION

(75) Inventors: Piran Sioshansi, Lincoln, MA (US); Raymond J. Bricault, West Boylston, MA (US)

(73) Assignee: Ion Beam Applications S.A., Louvain-la-Neuve (BE)

( * ) Notice: Subject to any disclaimer, the term of this patent is extended or adjusted under 35 U.S.C. 154(b) by 1892 days.

(21) Appl. No.: 10/284,037

(22) Filed: Oct. 29, 2002

(65) Prior Publication Data

US 2004/0073107 A1   Apr. 15, 2004

Related U.S. Application Data

(60) Provisional application No. 60/418,064, filed on Oct. 11, 2002.

(51) Int. Cl.
*A61B 5/05* (2006.01)

(52) U.S. Cl. ........ 600/414; 600/420; 600/426; 600/431; 424/9.1

(58) Field of Classification Search .............. 600/3, 407, 600/424, 439, 414, 420, 426, 431; 424/9.1
See application file for complete search history.

(56) References Cited

U.S. PATENT DOCUMENTS

| | | | |
|---|---|---|---|
| 5,221,269 A | 6/1993 | Miller et al. | |
| 5,234,426 A | 8/1993 | Rank et al. | |
| 5,810,007 A | 9/1998 | Holupka et al. | |
| 6,136,015 A * | 10/2000 | Kurz et al. | 606/191 |
| 6,165,178 A * | 12/2000 | Bashiri et al. | 606/108 |
| 6,168,570 B1 * | 1/2001 | Ferrera | 600/585 |
| 6,228,055 B1 | 5/2001 | Foerster et al. | |
| 6,241,691 B1 * | 6/2001 | Ferrera et al. | 600/585 |
| 6,254,592 B1 | 7/2001 | Samson et al. | |
| 6,356,782 B1 | 3/2002 | Sirimanne et al. | |
| 6,371,904 B1 * | 4/2002 | Sirimanne et al. | 600/3 |
| 6,419,621 B1 | 7/2002 | Sioshansi et al. | |
| 6,424,856 B1 * | 7/2002 | Vilsmeier et al. | 600/426 |
| 6,425,903 B1 | 7/2002 | Voegele | |
| 6,436,026 B1 | 8/2002 | Sioshansi et al. | |
| 6,468,266 B1 * | 10/2002 | Bashiri et al. | 606/1 |
| 6,475,169 B2 * | 11/2002 | Ferrera | 600/585 |
| 6,497,671 B2 * | 12/2002 | Ferrera et al. | 600/585 |
| 6,725,078 B2 * | 4/2004 | Bucholz et al. | 600/410 |
| 7,070,608 B2 * | 7/2006 | Kurz et al. | 606/200 |

(Continued)

FOREIGN PATENT DOCUMENTS

JP    08-112356 A    5/1996

(Continued)

OTHER PUBLICATIONS

European Extended Search Report, European Patent Application 10185030.3, date of completion of search Jan. 25, 2011, 3 pages.

(Continued)

*Primary Examiner* — Sanjay Cattungal

(74) *Attorney, Agent, or Firm* — Fitch, Even, Tabin & Flannery

(57) ABSTRACT

The present invention is related to an interstitial marker for localizing an organ, tumor or tumor bed within a mammalian body wherein said marker has a proximal end, a distal end, and a continuous intervening length, at least a portion of the intervening length of said marker being visible under at least one imaging modality and having a flexibility such that said marker follows movements and changes of shape of said organ, tumor or tumor bed.

25 Claims, 9 Drawing Sheets

– Diagram of a typical elongated marker coil

U.S. PATENT DOCUMENTS

| | | | |
|---|---|---|---|
| 7,318,805 B2 * | 1/2008 | Schweikard et al. | 600/439 |
| 2004/0109823 A1 * | 6/2004 | Kaplan | 424/1.11 |
| 2005/0038467 A1 * | 2/2005 | Hebert et al. | 606/194 |
| 2006/0074443 A1 * | 4/2006 | Foerster et al. | 606/185 |

FOREIGN PATENT DOCUMENTS

| | | |
|---|---|---|
| WO | WO 00/67202 | 11/2000 |
| WO | WO 02/41786 | 5/2002 |

OTHER PUBLICATIONS

International Search Report, International Patent Application PCT/BE2003/000171, date of the actual completion of the international search Feb. 5, 2004, 4 pages.

Civco Medical Solutions, Fiducial Marker Kit, http://www.civco.com/oncology/localization/fiducial-gold/, 3 pages, the product believed to be mentioned in the provisional application filed Oct. 11, 2002.

Iodine-125 and Palladium-103, Patented Double Wall Best® Iodine-125 Source Model #2301, Best Medical International, Inc., Springfield, Virginia, 5 pages, the product believed to be mentioned in the provisional application filed Oct. 11, 2002.

Biopsy and Special Purpose Needles: Disposable Kopans Breast Lesion Localization Needles, 1 page, the product believed to be mentioned in the provisional application filed Oct. 11, 2002.

Biopsy and Special Purpose Needles: Disposable Interventional MReye™ Needles for Magnetic Resonance Imaging, 1 page, the product believed to be mentioned in the provisional application filed Oct. 11, 2002.

Biopsy and Special Purpose Needles: Centimeasure™ Biopsy Depth Marker, 1 page, the product believed to be mentioned in the provisional application filed Oct. 11, 2002.

* cited by examiner

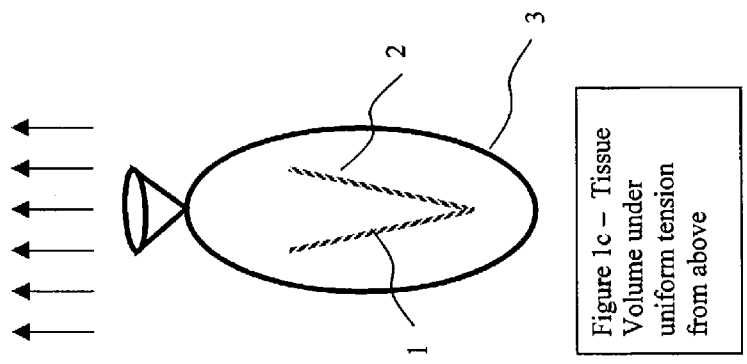
Figure 1c – Tissue Volume under uniform tension from above
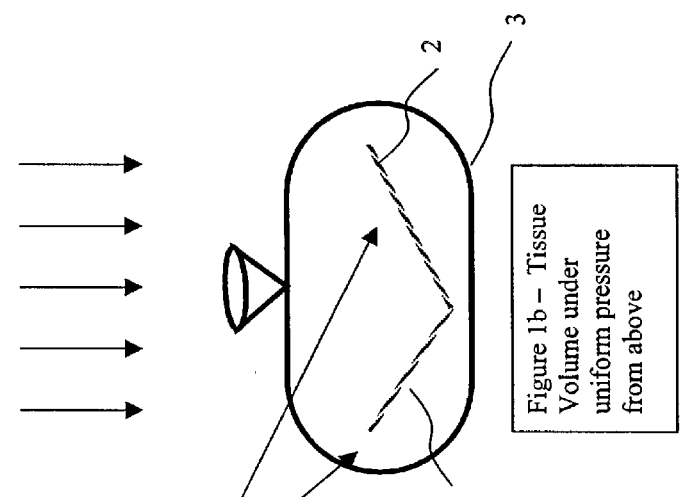
Figure 1b – Tissue Volume under uniform pressure from above
Marker wires 1, 2
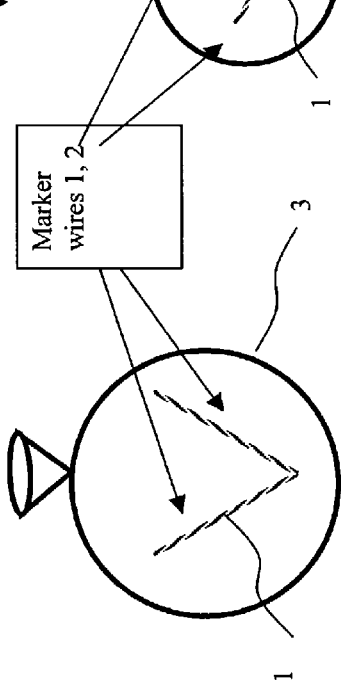
Figure 1a – Normal Tissue Volume
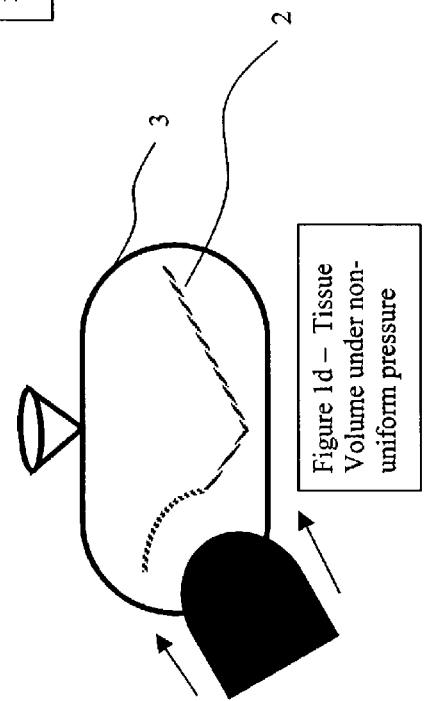
Figure 1d – Tissue Volume under non-uniform pressure

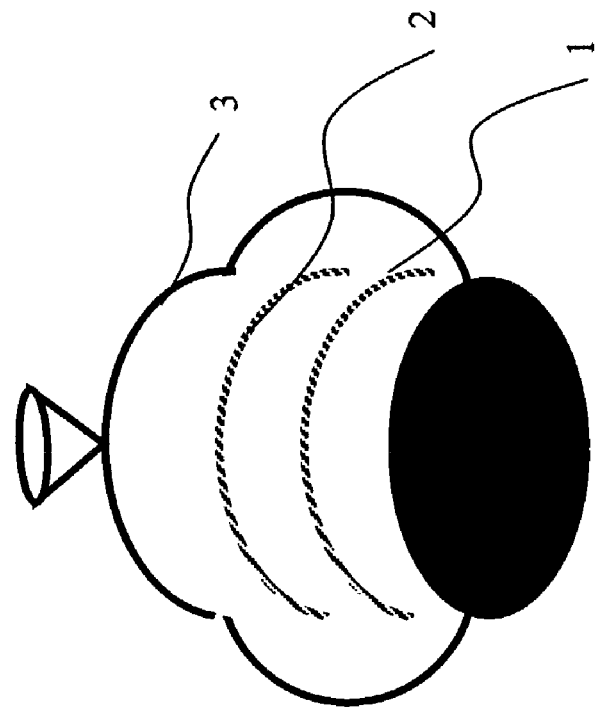
Figure 2b – Tissue with Parallel Marker, Pressure or growth from beneath
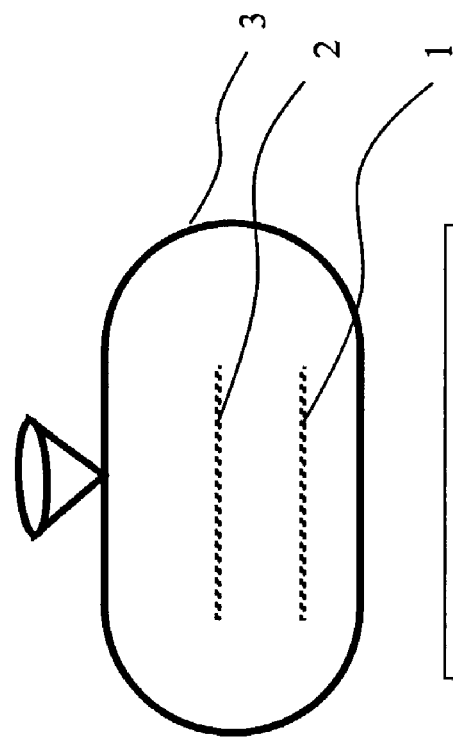
Figure 2a – Normal Tissue with Parallel Marker

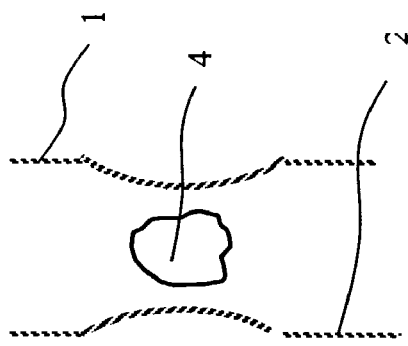
Figure 3c – Parallel Markers Adjacent to an existing tumor showing marker reaction to tumor shrinkage
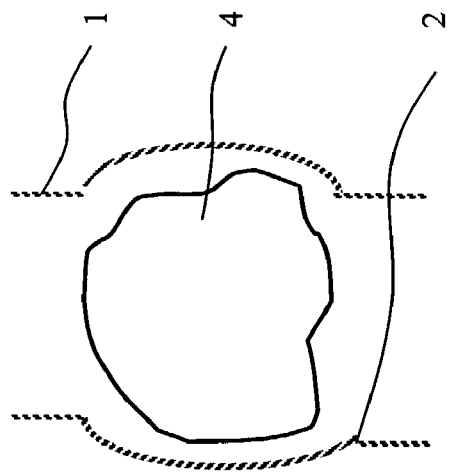
Figure 3b – Parallel Markers Adjacent to an existing tumor showing marker reaction to tumor growth
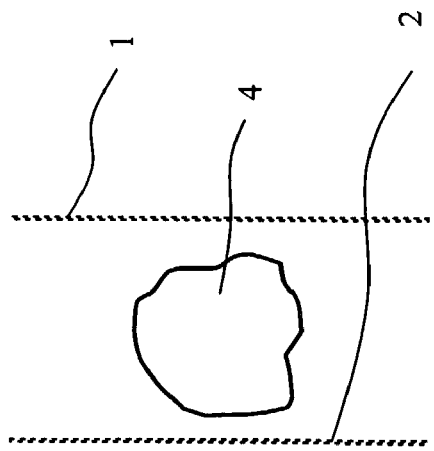
Figure 3a – Parallel Markers Adjacent to an existing tumor or tissue volume

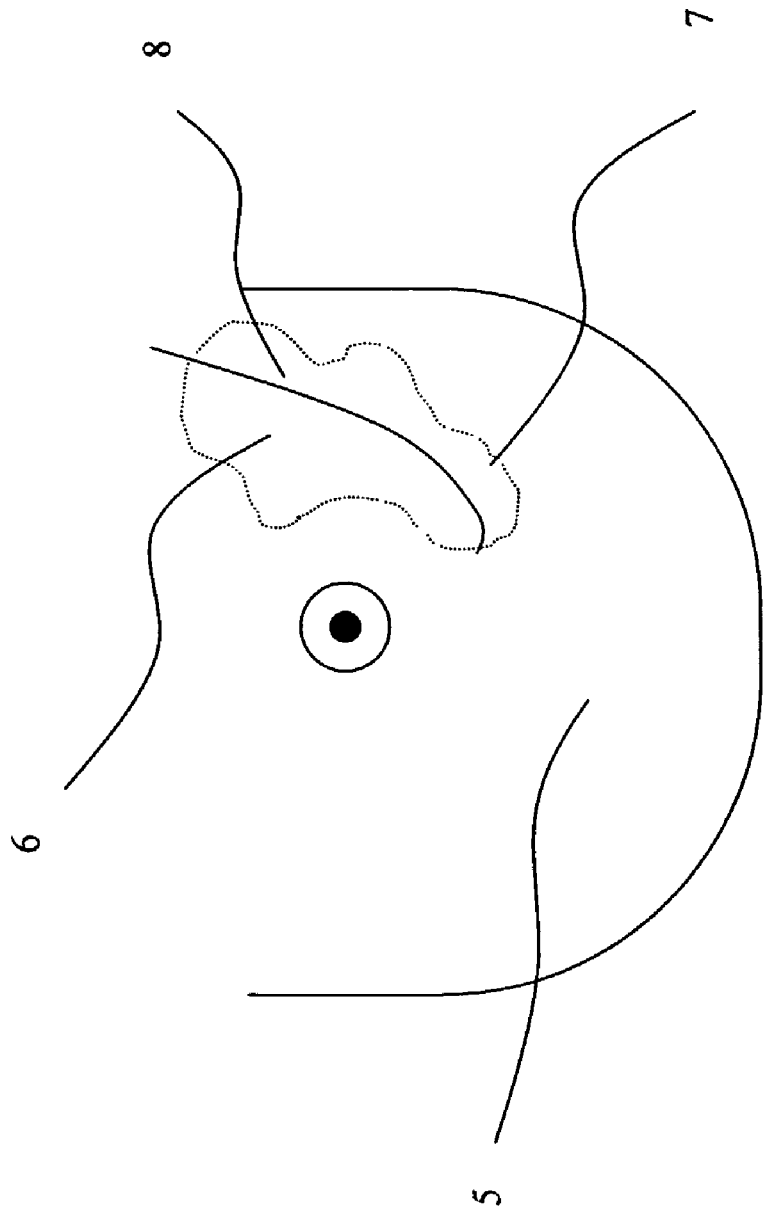
Figure 4 – Representation of a human Breast indicating the subsurface void formed by the lumpectomy. The surgeon would have the option of deploying a continuous length of marker around the periphery of the void (excision bed) or several lengths placed strategically about the bed itself

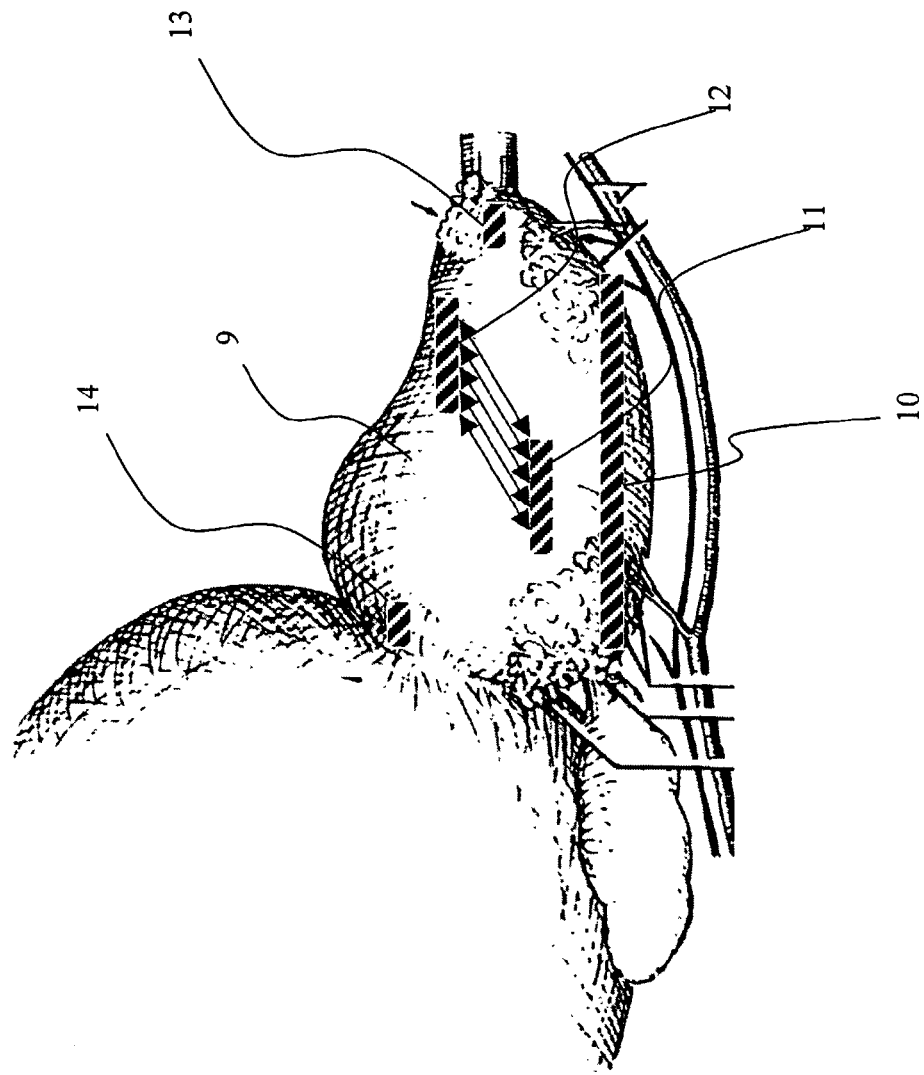
Figure 5 – Schematic representation of 1 scheme for the use of elongated markers to identify current size, shape and position of the prostate and to identify any potentials changes to the gland before, during or after a radiotherapy procedure.

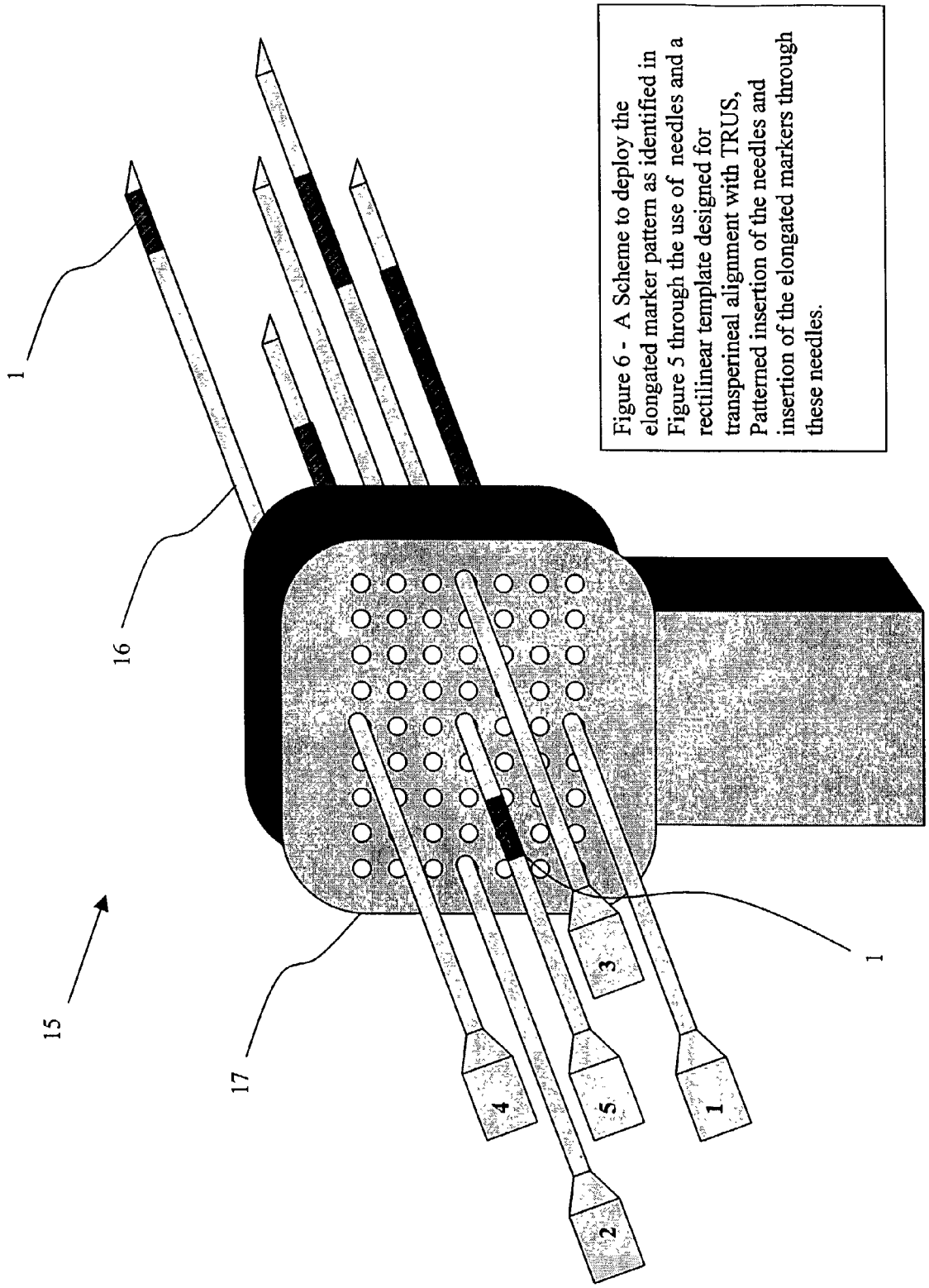
Figure 6 - A Scheme to deploy the elongated marker pattern as identified in Figure 5 through the use of needles and a rectilinear template designed for transperineal alignment with TRUS, Patterned insertion of the needles and insertion of the elongated markers through these needles.

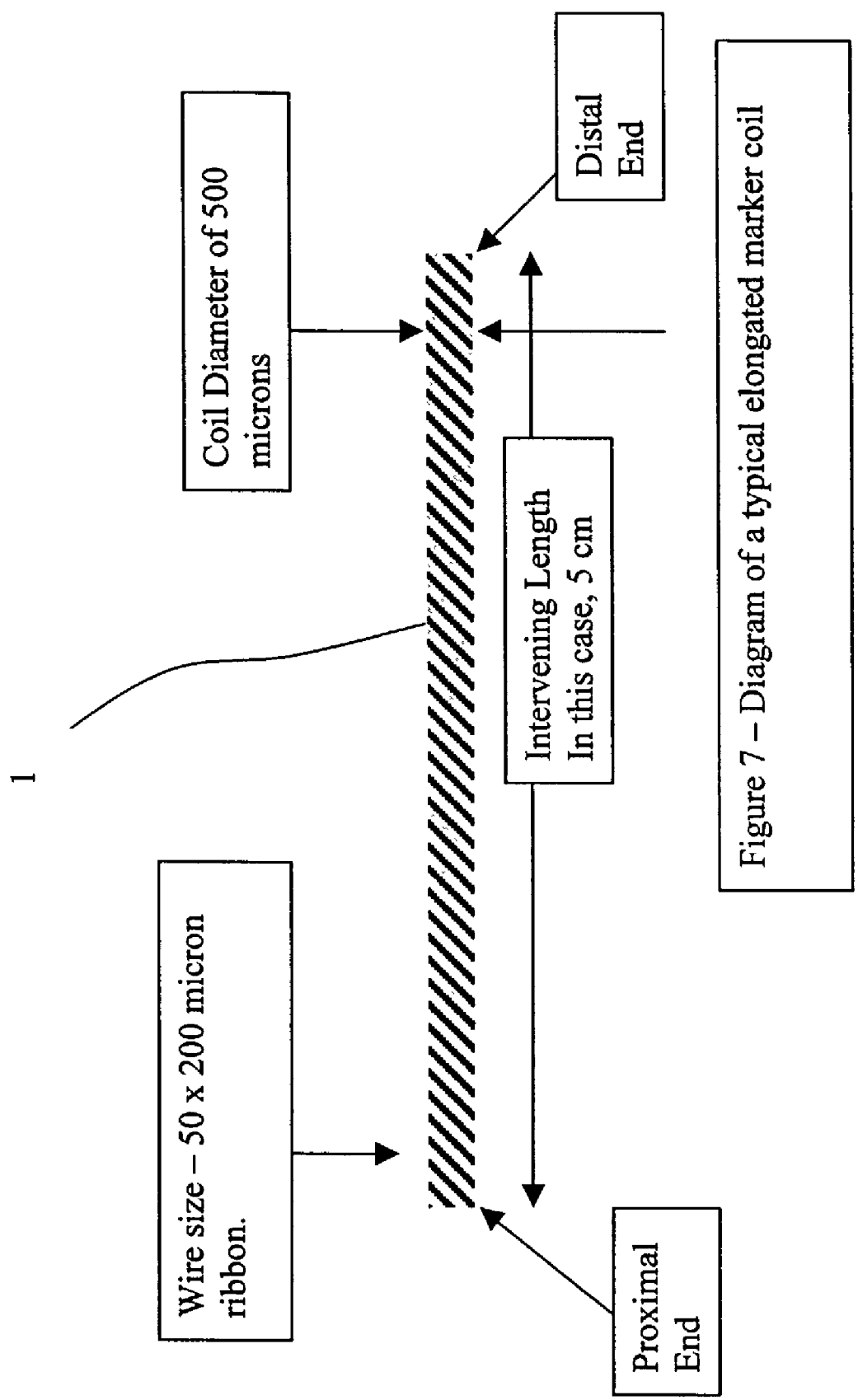
Figure 7 – Diagram of a typical elongated marker coil

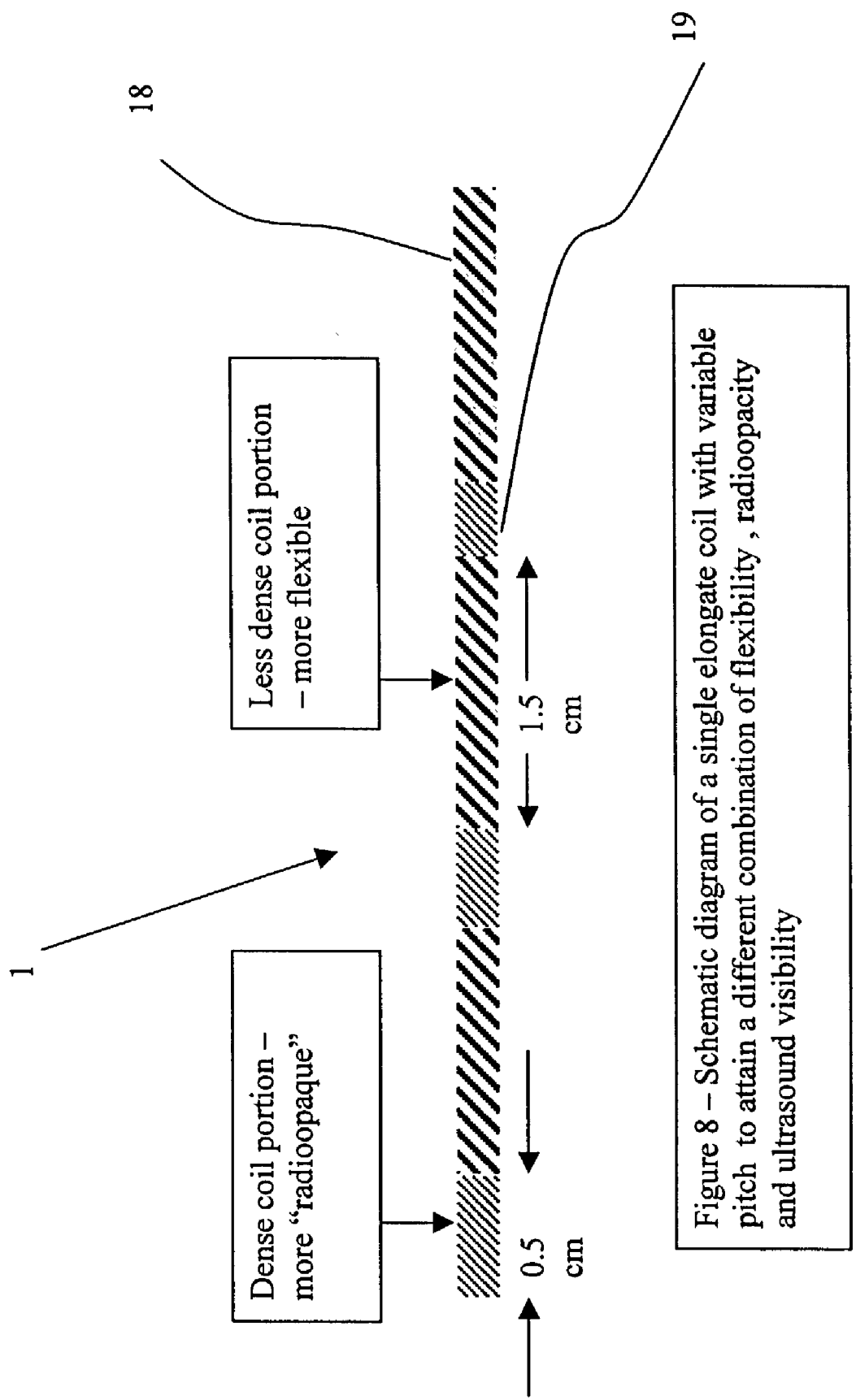
Figure 8 – Schematic diagram of a single elongate coil with variable pitch to attain a different combination of flexibility, radioopacity and ultrasound visibility

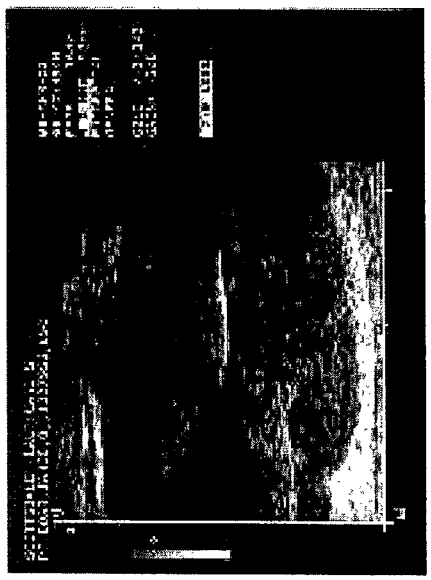
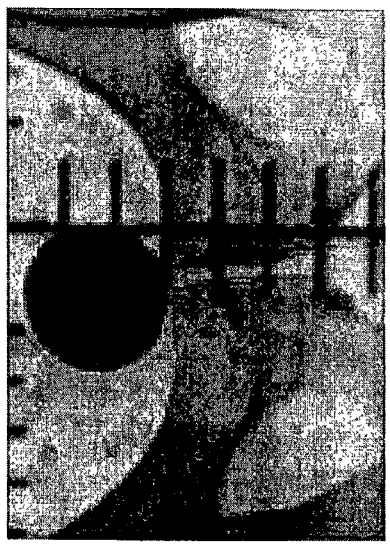
Figures 9a-d – Images of the marker coils of the current invention obtained from various imaging techniques a)Fluoroscope, b) CT, c) x-ray, d) ultrasound.

ELONGATED MARKERS FOR SOFT TISSUE VOLUME IDENTIFICATION

This application is related to and claims priority to Ser. No. 60/418,064, filed on 11 Oct. 2002, entitled: ELONGATED MARKERS FOR SOFT TISSUE VOLUME IDENTIFICATION, which application is specifically incorporated by reference herein.

FIELD OF THE INVENTION

The present invention is related to a device and method for marking, localizing and tracing the absolute position, motion and/or distortion of organs and regions or voids in organs, particularly in flexible tissue in human and animal subjects. The invention is further related to methods of use of the device of the invention.

STATE OF THE ART

Interstitial markers are used in many medical applications for localizing and following-up regions of body.

A first typical application of interstitial markers is in the following context: a tissue abnormality is detected by a known diagnostic tool, such as ultrasonography, PET, SPECT, CT scan, mammogram, radiography or manual palpation. The diagnostic tool does not allow making a distinction between a malignant and a benign tumor. A biopsy is performed in order to analyze the tumor. A marker is then inserted at the location of the biopsy, for later precise treatment of the tumor, if necessary. Breast cancer diagnosis and treatment require such markers.

In another application, interstitial markers are also used for preparing patients undergoing radiation treatment such as proton beam, electron beam or x-ray treatments. Such treatments are usually split in a sequence of daily sessions or fractions. A treatment might for example be delivered in 25 days, each giving a dose of 3 Gy. In order to precisely position the patient with respect to the irradiation source, it is necessary to have markers that are visible to the eye or to an X-ray imaging system. For tumors that are in a fixed position with respect to bone structures, e.g. tumors in the brain, these bone structures can be used as markers. However, for soft tissues, which are not in a fixed position with respect to bone structures, these markers are of no avail. This is the case for the breast and the prostate, for which it has been determined that average movement may be as large as 30 mm. With irradiation techniques such as proton or heavy ion therapy or IMRT allowing 3D conformation of the applied dose to the target tumor, a marker and method for marking are needed for aligning the tumor to be treated with the treatment beam. Irradiation techniques have been improved, and accuracy better than 1 mm in beam spatial position is now state of the art so a corresponding precision in patient positioning is required.

In still another application, there is a need for means for following up the growth or decrease in size of a tumor. With the known interstitial markers, such as seeds, it is possible to follow the position of the markers, and hence of the organ in which they are embedded. It is however not possible to follow the change of shape of said organ. Typical seeds do move 2-3 mm on average from the position to which they were deployed. Marker migration cannot be distinguished from organ displacement or distortion. Fundamentally, with point markers, clinicians are left to impute the behavior of the tissue between two or more markers. There is typically no detailed knowledge of the behavior of the tissue between the markers. This can lead to misinterpretation of the target volume change or deformation if the tissue or organ is being subjected to either external or internal forces.

It has been determined that, for the treatment of some cancers such as prostate cancers, a combination of several treating methods produces the best results. In prostate cancer therapy, a combination of brachytherapy, i.e. inserting radioactive implants into the organ, and external beam therapy give good results. The brachytherapy implants traditionally used are seeds having the shape and size of a grain of rice. However, such seeds have two drawbacks: they can drift away from their intended location, and they give poor visibility to ultrasound imaging.

The need for an interstitial marker appears in the diagnosis and treatment of cancers such as breast and prostate cancer. It is preferred that these markers be readily visible to the imaging techniques used. They must therefore be visible to X-rays, used in the mammogram. They also must be visible under ultrasonoscopy or ultrasonography, and therefore have a good "echogenicity", i.e. reflect ultrasounds.

Document U.S. Pat. No. 5,221,269 discloses a marker wire for localizing a breast lesion. The marker wire is made of a superelastic material, and preformed into a helical coil configuration. The marker wire is introduced trough a tubular needle, straightened out, and regains its helical shape when pushed out of the needle. The diameter of such coil is typically 3 cm, and the wire used has a diameter of 300 μm. The proximal end of the wire, when the marker is installed, appears at skin level. This marker can therefore only be used for short term marking, between biopsy and treatment, and may not be left permanently in the body. The distal end of the needle used for introduction may include a plurality of semi-spherical indentations in order to enhance the ultrasound visibility.

Document U.S. Pat. No. 5,234,426 discloses a marker made from a shaft, and having, at its distal end, a helicoidally wound wire. The wire has a diameter of between 0.009 and 0.015 inches (between 200 and 400 μm). This marker, when positioned, also has a proximal end protruding from the patient's body.

Document U.S. Pat. No. 6,228,055 discloses i.a. the use of embolization coils as marker. Embolization coils are designed for permanent placement into veins or arteries for curing of vascular lesions or malformations. Such intraluminal devices have an external diameter adapted to the vessel to be treated, typically of the order of magnitude of 0.5 to 5 mm, and made of a material and size giving sufficient mechanical strength to perform their function. Document WO 02/41786 also discloses the use of an embolization coil as a biopsy marker. These devices have, as a result of their size and rigidity, many drawback for use as interstitial markers: (i) they can not be introduced through a minimally invasive intervention, such as a fine needle; (ii) they may not be readily accepted as permanent marker, left in the body, in case the biopsy does not reveal the tumor to be malignant; (iii) they lack the lateral and axial flexibility that is required for permanent insertion in soft tissues that may shrink or swell under the influence of outside factors; (iv) they may mask and conceal features of the lesion that should remain visible to the therapist.

For marking biopsy sites, e.g. for breast biopsies, it is known to use clips, such as the one disclosed in document U.S. Pat. No. 6,425,903. The placement of a set of such clips does not allow the follow-up of the shape of the cavity. It is also known to use a combination of a filler body, and a detectable marker, as know from document U.S. Pat. No.

6,356,782. The presence of a filler body may not improve the healing process of the biopsy site.

Through the development of medical imaging techniques, such as digital X-ray radiography, mammography, CT (computerised tomography) scan, MRI(magnetic resonance imaging), Ultrasonography, PET (positron emission tomography) scan, means for detecting detailed features of organs and tumors are now available. Each of these techniques have their advantages, drawbacks and preferred fields of application. Spatial resolution, capability of tissue differentiation, trauma to the patient, speed and cost may vary. It is therefore desirable to be able to reconcile data obtained from these different imaging techniques, or from images taken through the same techniques from different angles and or at different times. A method for fusion of images obtained through x-rays and ultrasound is known from document U.S. Pat. No. 5,810,007. In this method, the fiducials (reference points) used for superposing both images are part of the ultrasound probe. The precision of the process relies on the precise location of the ultrasound probe, and cannot be used to fuse images taken at different times, the ultrasound probe, being removed.

It is therefore an object of the present invention to provide a marker that is small and flexible enough to be permanently left in the patient body, that can be inserted through a minimally invasive technique, that can show organ change of shape, and that is readily visible under imaging techniques, including x-ray and ultrasound, during and after insertion.

It is another object of the present invention to provide method for precisely localising an organ or tumor to be treated with a radiation beam, and a marker adapted for use in said method.

It is still another object of the present invention to provide a method for following-up the location, change of size of an organ or tumor, and a marker adapted for use in said method.

It is also an object of the present invention to provide a method of image fusion, and a marker adapted for use in said method.

SUMMARY OF THE INVENTION

The present invention is related, in one aspect, to an interstitial marker for localizing an organ, tumor or tumor bed within a mammalian body. The marker has a proximal end, a distal end, and a continuous intervening length. At least a portion of the intervening length is visible under at least one imaging modality and has a flexibility such that said marker follows movements and changes of shape of said organ, tumor or tumor bed. In a preferred embodiment, the interstitial marker has a ratio of said length to its diameter of 10 or higher. Depending on the application, said ratio may even be of 250 or higher. The interstitial marker may comprise a flexible wire, and said wire may be in form of a helical coil, whereby an advantageous flexibility is obtained. The helical coil marker may comprise sections of different pitch. Sections of different pitch have different characteristics as to visibility under different imaging modalities, and also have different mechanical characteristics as to longitudinal and lateral flexibility. At least portions of the marker may be made of a radiopaque material. They may be visible under diagnostic x-ray imaging, eg x-rays having an energy in the range of 100 keV. They may also advantageously be visible under higher energy x-rays used in treatment beams, eg x-rays in the range of 3 to 50 MeV. They also preferably may be visible under ultrasound imaging. The marker may include one or more tissue anchors at opposite ends thereof, and/or at intermediate points to fix the marker in the organ, tumor or tumor bed. The marker will thereby follow changes of size and shape, especially longitudinal size changes. Other means for anchoring to said organ, tumor or tumor bed may be used, e.g. a structure of the lateral surface of the marker improving the grip of the marker to the tissue, such as the ridges on the outer surface of an helical coil. The marker is preferably made of a biocompatible material suitable for permanent implantation. Such material may be rhodium, platinum, iridium, tantalum, titanium, silver, gold, nickel, alloys containing these metals and stainless steel.

According to another aspect of the invention, method is provided for treating a soft tissue organ, tumor or tumor bed of a patient with a radiation beam, using a beam delivery setup, wherein a prescribed dose is delivered in one or more fractions. One inserts one or more markers of the invention in the organ, tumor or tumor bed. One then roughly positions the patient for receiving the radiation beam and then forms an image of the marker or markers under an imaging modality, eg x-ray image. From the image or images, one can infer the exact position, shape and change of shape of said organ, tumor or tumor bed. One can then adjust patient position and/or radiation beam delivery setup in order to direct the radiation beam towards the organ, tumor or tumor bed, and delivering the treatment beam exactly to the precise organ location, size or orientation. If the prescribed dose is to be delivered in successive fractions, one can repeat the above steps, adapting each time the patient position and beam delivery setup according, when the organ to be treated changes position, size and/or orientation during the treatment.

A further aspect of the invention is related to a method of determining the change of shape, size or location of an organ, tumor or tumor bed. One or more markers of the invention are inserted in the organ, tumor, or tumor bed. The markers have flexibility such that they follow movements and changes of shape of the organ, tumor or tumor bed. The length of the marker may be chosen according to the size of the organ, tumor or tumor bed to be followed. Successive images of the organ are taken. From the change of shape or position of said markers, one infers the change of shape, size or location of the organ, tumor or tumor bed.

In a further aspect of the invention, a method comprises the insertion of two or more markers in said organ, tumor, or tumor bed. Additional information may be obtained from the relative distance, relative orientation and change of shape or position of the two or more markers.

According to another aspect of the invention, a method is provided for determining the change of shape, size or location of an excision cavity. Having performed an excision, the surgeon positions one or more markers of the invention along a periphery of the excision cavity. The flexibility of the markers of the invention is such that the markers can readily be adapted along the periphery of the excision. The markers can be sutured in place or anchored by means of their tissue anchors. By taking successive images, one can infer the change of shape, size or location of the excision cavity from the change of shape or position of the markers.

According to another aspect of the invention, a method is provided for marking boundaries of anatomical regions in a mammalian body. One obtains a real-time image pursuant to an imaging modality, e.g. ultrasonoscopy, or fluoroscopy, showing the anatomical regions on a display, on which the boundaries of said anatomical regions can be identified. One inserts one or more markers of the invention, guided by the real time-display, positioning distal and/or proximal ends of the markers at boundaries of the anatomical regions of interest. In a preferred embodiment of said method, the anatomical region of interest is the prostate region, and the boundaries include the prostate apex, the prostate base, the prostate-rectum boundary, the lateral boundaries of the prostate, and the boundaries of the colon, the urethra, the bladder, the seminal vesicles, the neurovascular bundles and the penile bulb. The real-time image may advantageously be obtained through a transrectal ultrasound probe.

According a further aspect of the invention, a method is provided for fashioning a plurality of images obtained trough one or more imaging modalities (e.g. X-ray radiography, CT-scan, Ultrasonography), of an anatomical region. One inserts one or more markers of the invention in or near the anatomical region of interest. One obtains images of the anatomical region, showing i.a. the markers of the invention. The images are then processed for modifying the scales and orientations so as to align the sizes, shapes and positions of the markers in each of the images.

In a variation of the method for fusioning images, one inserts two or more markers in or near the anatomical region. One can then use the relative distances and relative orientations of the two or more markers for modifying the scales and orientations of the images.

SHORT DESCRIPTION OF THE DRAWINGS

FIG. 1a to 1d show how a pair of markers according to the invention can be used to follow the change of shape of an organ.

FIGS. 2a and 2b show a pair of parallel markers according to the invention can be used to follow the change of shape of an organ.

FIG. 3a represents an organ after insertion of an interstitial marker. FIG. 3b represents same organ and markers after increase in size of part of organ, and FIG. 3c represents same organ and markers after decrease in size of organ.

FIG. 4 shows a marker inserted as used for marking a biopsy site.

FIG. 5 is a schematic representation of a set of markers inserted into a prostate.

FIG. 6 is a perspective view of an apparatus used for positioning a set, of markers into a prostate.

FIG. 7 is a side view of a marker according to invention, where the marker is a helical coil, having a constant pitch.

FIG. 8 is a side view of a marker according to the invention, where the marker is a helical coil, having sections of high pitch and sections of low pitch.

FIG. 9a-9d are images of the marker according to the invention, obtained from various imaging techniques.

DETAILED DESCRIPTION OF THE INVENTION

The coiled marker of the invention is of such flexibility, both axially and transversally, so that, when inserted in a flexible organ such as a breast or a prostate, it will follow the changes of shape of said organ. The lateral flexibility of the markers must be similar to the flexibility of the tissues in which they are inserted. The coiled marker does not present any mechanical resistance to the change of shape. After insertion through a needle, the marker is largely straight. When the organ changes in shape, either under the influence of the treatment, or under natural growth or stresses, the flexible markers will take a curved shape. It has been experienced that the coiled markers grip the organ they are inserted into, and follow the longitudinal change of shape. One can therefore follow the change of shape and relative position of markers for following increase in size and change of shape of the organ. The fact that the markers of the invention have an excellent ultrasound visibility means that these repeated examination may be performed with the ultrasound technique, thereby avoiding the doses of repeated X-ray exposures.

The implantation of two or more coiled markers in an organ allows following the position of the organ in the body. This is especially necessary for flexible organs such as breast or prostate. Depending on contents of bladder or colon, the prostate may be displaced by several cm. Treatment by an external beam may be directed with a precision better than 1 mm.

FIG. 1a, 1b, 1c 1d illustrate how the change of shape of an organ can be followed using the markers of the invention. In FIG. 1a, two markers 1, 2 have been inserted into an organ 3 (symbolized here as a gel-filled balloon). The markers are straight after insertion. In FIG. 1b, the organ has been submitted to a uniform pressure from above, and the change in shape of the organ can be inferred from the change in relative orientation of the markers. Similarly, in FIG. 1c, the organ has been submitted to a uniform tension from above, and the markers show a corresponding change in relative position. In FIG. 1d, the organ has been submitted to a non uniform pressure, e.g. due to stresses within the body (full bladder or stomach, gas, swelling, etc), stresses from localized growths (tumors), external stresses (clothing or hardware in contact with the patient), changes in weight, changes in hydration, etc. These are reflected in the change of shape of the intervening length of marker 1.

The use of two or more interstitial markers of the invention inserted parallel allow even better follow-up of the change of shape, as shown on FIGS. 2a and 2b.

As illustrated on FIGS. 3a, 3b, and 3c, the evolution of an organ or tumor can be followed using the interstitial markers of the invention. In FIG. 3a, one or more markers have been inserted parallel and straight around a region of interest 4. Subsequent images are taken after a period and can show growth (FIG. 3b) or decrease in size (FIG. 3c) of the region of interest. It is to be emphasized that the imaging technique used for the follow-up must be able to see the markers, but do not have to be able to see the region of interest. Therefore, an imaging technique that is faster, less invasive, or more comfortable for the patient can be used. Especially, the ultrasound imaging technique can be used.

Another application of the interstitial marker according to the invention is the marking of an "excision bed". Specifically, in numerous medical procedures a volume of tissue is surgically removed, such as in the case of a lumpectomy. In many of these cases it is important to be able to return to this same tissue volume for follow-up procedures such as radiation therapy, additional surgical excision, etc. As this "empty" volume is ill defined until the healing process is complete, elongated flexible markers placed in the tissue immediately adjacent to this volume can provide a detailed description of the location. In this case, point markers suffer the same deficiencies as identified above for soft tissue or tumor volume marking with the added issue that the typical 2-3 mm migration can cause the marker to fall into the excision volume and simply be "floating" in this tissue void. The extended length of the interstitial marker according to the invention eliminates this possibility. In these cases, the elongated marker could be either inserted into the target tissue or sutured in place in cases where an open surgical procedure has been used. FIG. 4 represents a human breast 5 indicating the subsurface excision bed 6 (void formed by the lumpectomy), and the skin-level surgical scar 8. The surgeon would have the option of deploying a continuous length of marker 7 around the periphery of the excision bed or several lengths placed strategically about the bed itself.

The marker according to the invention is particularly useful in the external beam therapy of prostate cancer. Patients who have been diagnosed with prostate (or other) cancer have a number of surgical (radical prostatectomy or other surgical excision of the affected tissue) and non-surgical options to evaluate for their treatment. These non-surgical options include radiation therapy options, hormone therapy, hypothermia, hyperthermia, drugs and genetic therapy. To date, only radiation therapy and surgical removal have shown 10-year disease free survival rates above 80% and represent the standard of care in the industry. Of the radiation therapy options, the optimal goal is to deliver as much radiation (up to the prescribed dose) as possible to the organ (in this case prostate) and as little radiation as possible to all the surrounding tissues to reduce the comorbidity (or side effects) of this procedure. As a result, the progression of external beam radiation therapy over the past two decades has been focused on providing a beam of radiation that matches the shape of the organ. With each passing year, publications show advances in being able to target the radiation in more effective ways and continually lessening the dose to adjacent tissues. At this point in time, the most accurate of these therapies (proton therapy) claim the ability to localize the beam to 0.1 mm of the intended target location.

FIG. 5 illustrates the method for marking the boundaries of anatomical regions, with the application to the prostate 9. Elongated marker 10 has been inserted in the prostate, near the prostate/rectum boundary. Such marker may typically have a length of 4 cm, and is used for height adjustment. Elongated markers 11 and 12 are located at the left and right hand side of the prostate, and delimit the lateral width of the gland in the mid-plane. These markers are used in conjunction with marker 10 for left-right alignment. Marker 13 defines the prostate apex, and is used for cranial-caudal adjustment of patient position. Marker 14 defines the prostate base, and is used also for cranial-caudal adjustment. Once in place, these markers will follow the change of position, size and orientation of the gland, and thereby allow follow-up of the decrease or increase in size of the organ, and allow precise positioning and directing during radiation beam treatment.

FIG. 6 illustrates a known device 15 used to deploy the elongated marker pattern identified in FIG. 5 through the use of needles 16 and a rectilinear template 17 designed for transperineal alignment with TRUS (transrectal ultrasound), and a method of patterned insertion of the elongated markers 1 through these needles, with pusher wires. Prostate markers may also be inserted digitally through the rectum and positioned with tactile guidance and/or ultrasound imaging guidance.

FIG. 7 represents a coiled marker 1, having an outer diameter of 500 μm (0.5 mm), made of thin wire having a rectangular section of 50×200 μm, coiled with the broad side along the axis of the coil, and having a length of 5 cm. The length of the marker may be chosen as required by the application, and may be as short as 1 cm for marking the longitudinal ends of an organ, as in the case of prostate apex and base, and as long as necessary, e.g. for biopsy sites, where lengths of 10 cm or more may be used. Depending on the application, the outer diameter may be chosen between 25 μm and 2500 μm, and the wire may have a circular cross section with a diameter between 10 μm and 2500 μm or a rectangular cross section with sizes between 10 μm and 500 μm. The aspect ratio i.e. the ratio of length to outer diameter in the example shown is 100, but it has been determined that an aspect ratio in the range on 10 to 250 or higher provides a good combination of flexibility and x-ray and ultrasound visibility. Another characteristic feature of a helical coil is the pitch, that may be defined as the axial length between two successive coil windings.

Other examples of coils suitable for particular applications are given below:

Example 1

Primarily Designed for Use with Ultrasound or Diagnostic X-Ray Imaging Techniques

| Material | Rhodium |
| --- | --- |
| Helix Outer Diameter | 350 μm |
| Helix Inner Diameter | 250 μm |
| Rectangular wire, size | 200 × 50 μm |
| Wire Pitch | 240 +/− 40 μm |

Example 2

Designed Primarily for Diagnostic X-Ray, Fluoroscope or Ultrasound

| Material | Platinum |
| --- | --- |
| Helix Outer Diameter | 500 μm |
| Helix Inner Diameter | 350 μm |
| Circular wire | 75 μm diameter |
| Wire Pitch | 90 +/− 9 μm |

Example 3

Primarily Designed for Portal Imaging

High Energy X-Rays

| Material | Gold |
| --- | --- |
| Helix Outer Diameter | 2.0 mm |
| Helix Inner Diameter | 1.2 mm |
| Wire Diameter | 0.4 mm |
| Wire Pitch | 0.48 +/− 0.08 mm |

The lateral flexibility obtained by using a coil according to the invention is very high. This flexibility is easily determined by measuring the droop of a length of helical coil fastened horizontally from one end. The other end droops in response to its own weight. It was determined that a coil made of stainless steel, having an outer diameter of 350 μm, a rectangular cross section wire of 200 μm by 50 μm, a 220 μm pitch, and a free length of 35.5 mm, droops by 2.9 mm.

FIG. 8 represents a preferred embodiment of a coiled marker 1, having sections of different pitch. Sections of high pitch 18 (less dense coils) provide a good flexibility, while sections of low pitch 19 (dense coils) provide good x-ray and ultrasound visibility.

FIG. 9a-9d represent images of the marker coils of the present invention obtained from various imaging techniques: fluoroscopy (FIG. 9a), CT (FIG. 9b), x-ray (FIG. 9c) and ultrasound (FIG. 9d).

It has been discovered by the inventors of the present invention that a helical coil, such as disclosed in U.S. Pat. No.

6,419,621, which is incorporated herein by reference, can effectively be used as an interstitial marker according to the invention. More precisely, said document discloses a radioactive coiled wire. These radioactive coiled wires are obtained through an activation process that may be exposure to an accelerated beam of charged particles of a precursor material, through ion implantation technique, or through thin film deposition of an isotope. The coil that can be used as interstitial marker is the coil prior to activation. This allows using same material for use as an interstitial marker as well as precursor for making a brachytherapy device. These coils may also be used after activation, and be used simultaneously as a brachytherapy device and as a marker, for a combined brachytherapy/external beam irradiation treatment.

We claim:

1. A method for treating a soft tissue organ, tumor or tumor bed of a patient with a radiation beam, using a beam delivery setup, wherein a prescribed dose is delivered in one or more fractions, comprising the steps of
   a) inserting one or more markers into soft tissue of the organ, tumor or tumor bed, the one or more markers having a proximal end, a distal end and continuous intervening length, the one or more markers configured to be held by the soft tissue and being visible under at least one imaging modality, the one or more markers markers comprising a single flexible wire in the form of a helical coil which is substantially linear just after insertion, the helical coil having a length and flexibility along the longitudinal axis of the marker and flexibility transverse to the longitudinal axis which flexibilities are effective to permit the marker to be responsive to changes of shape of the organ, tumor or tumor bed and to follow movements of the organ, tumor, or tumor bed after insertion into the soft tissue and while implanted in a patient;
   b) positioning the patient for receiving the radiation beam;
   c) forming one or more images of the one or more markers under one or more of the imaging modalities selected from the group consisting of x-ray, radiography, CT scan, ultrasonography, and fluoroscopy;
   d) inferring position, shape and change of shape of the organ, tumor or tumor bed from the one or more images;
   e) adjusting patient position and/or radiation beam delivery setup in order to direct the radiation beam towards the organ, tumor or tumor bed;
   f) delivering one of the treatment beam fractions; and
   g) repeating steps (b) to (f) until the prescribed dose is reached, wherein the marker comprising a non-radioactive helical coil having a length, diameter, a proximal end, a distal end, the coil configured for insertion into soft tissue inside the body and held by the soft tissue, the marker substantially straight just after insertion inside the soft tissue, the interstitial marker having a continuous intervening length, at least a portion of the intervening length of the marker being visible under at least one imaging modality selected from the group consisting of x-ray, radiography, CT scan, ultrasonography, and fluoroscopy, wherein the marker is a single flexible wire in the form of the helical coil having an outer diameter of from about 25 µm to about 2500 µm, a ratio of coil length to coil diameter of 10 or more and a wire diameter of from about 10 µm to about 2500 µm when the wire has a circular cross section or a wire rectangular cross section of from about 10 to about 500 µm, and a ratio of wire cross section width to helical pitch of about 1:1.2±about 0.2, the coil length, wire diameter, ratio of coil length to coil diameter and wire cross section effective for providing flexibility along the longitudinal axis, of the coil and flexibility transverse to the longitudinal axis which flexibilities are effective to permit the marker to be responsive to changes of shape of the organ, tumor or tumor bed and to follow movements of the organ, tumor, or tumor bed after insertion as a substantially straight coil, but after at least one of treatment, natural growth or stresses from the soft tissue while implanted in the mammalian body.

2. An interstitial marker configured to be imaged when positioned into soft tissue of an organ, tumor or tumor bed within a mammalian body, the marker comprising a non-radioactive helical coil having a length, diameter, a proximal end, a distal end, the coil configured for insertion into soft tissue inside the body and held by the soft tissue, the marker substantially straight just after insertion inside the soft tissue, the interstitial marker having a continuous intervening length, at least a portion of the intervening length of the marker being visible under at least one imaging modality selected from the group consisting of x-ray, radiography, CT scan, ultrasonography, and fluoroscopy, wherein the marker is a single flexible wire in the form of the helical coil having an outer diameter of from about 25 µm to about 2500 µm, a ratio of coil length to coil diameter of 10 or more and a wire diameter of from about 10 µm to about 2500 µm when the wire has a circular cross section or a wire rectangular cross section of from about 10 to about 500 µm, and a ratio of wire cross section width to helical pitch of about 1:1.2±about 0.2, the coil length, wire diameter, ratio of coil length to coil diameter and wire cross section effective for providing flexibility along the longitudinal axis, of the coil and flexibility transverse to the longitudinal axis which flexibilities are effective to permit the marker to be responsive to changes of shape of the organ, tumor or tumor bed and to follow movements of the organ, tumor, or tumor bed after insertion as a substantially straight coil, but after at least one of treatment, natural growth or stresses from the soft tissue while implanted in the mammalian body.

3. The interstitial marker according to claim 2 wherein the helical coil comprises sections of different pitch.

4. The interstitial marker according to claim 2 wherein at least portions of the marker are made of a radiopaque material.

5. The interstitial marker according to claim 2 wherein the marker is visible under x-ray imaging, wherein the x-ray imaging is diagnostic x-ray.

6. The interstitial marker according to claim 2 wherein the marker is visible under x-ray imaging, wherein the x-ray imaging is therapeutic high energy x-ray.

7. The interstitial marker according to claim 2 wherein the marker includes one or more tissue anchors.

8. The interstitial marker according to claim 2 wherein the marker comprises an anchoring portion configured for anchoring to the organ, tumor or tumor bed.

9. The interstitial marker according to claim 2 wherein the marker comprises biocompatible gold suitable for permanent implantation into a human.

10. The interstitial marker according to claim 2 wherein the marker comprises a material selected from the group consisting of-rhodium, platinum, iridium, tantalum, titanium, silver, gold, nickel, alloys of these metals, and stainless steel.

11. An interstitial marker configured to be imaged when positioned into soft tissue of an organ, tumor or tumor bed within a mammalian body, the marker comprising a non-radioactive helical coil having a length, diameter, a proximal end, a distal end and is configured for insertion into soft tissue of the organ, tumor or tumor bed and held by the soft tissue inside the body, the interstitial marker having a continuous intervening length, at least a portion of the intervening length of the marker being visible under at least one imaging modality selected from the group consisting of x-ray, radiography, CT scan, ultrasonography, and fluoroscopy, wherein the marker consists essentially of a single flexible wire in the form of the helical coil having an outer diameter of from about 25 µm to about 2500 µm, a ratio of coil length to coil diameter of 10 or more and a wire diameter of from about 10 µm to about 2500 µm when the wire has a circular cross section or a wire rectangular cross section of from about 10 to about 500 µm, and a ratio of wire cross section width to helical pitch of about 1:1.2±about 0.2, the coil length, wire diameter, ratio of coil length to coil diameter and wire cross section effective for providing flexibility along the longitudinal axis of the coil and flexibility transverse to the longitudinal axis which flexibilities are effective to permit the marker to be substantially linear just after insertion into the soft tissue and thereafter to be responsive to changes of shape of the organ, tumor or tumor bed and to follow movements of the organ, tumor, or tumor bed while implanted in the mammalian body.

12. The interstitial marker according to claim 11 wherein the helical coil comprises sections of different pitch.

13. The interstitial marker according to claim 11 wherein at least portions of the marker are made of a radiopaque material.

14. The interstitial marker according to claim 11 wherein the marker comprises biocompatible gold suitable for permanent implantation.

15. The interstitial marker of claim 11 wherein the ratio of the length of the coil to an outer diameter of the coil is from 10 to 250.

16. A method for observing changes in shape of an organ, tumor or tumor bed of a patient, the method comprising:
    inserting one or more non-radioactive helical coil markers in the organ, tumor or tumor bed, the one or more markers having a proximal end, a distal end and continuous length, the one or more non-radioactive helical coil markers being held by soft tissue of the organ, tumor or tumor bed, being substantially linear just after insertion and visible under at least one imaging modality, the one or more non-radioactive helical coil markers comprising a single flexible wire in the form of a helical coil with a longitudinal axis, the helical coil having a length, an outer diameter of from about 25 µm to about 2500 µm, a ratio of coil length to coil diameter of 10 or more and a wire diameter of from about 10 µm to about 2500 µm when the wire has a circular cross section or a wire rectangular cross section of from about 10 to about 500 µm, and a ratio of wire cross section width to helical pitch of about 1:1.2±about 0.2, the coil length, diameter, ratio of coil length to coil diameter and wire cross section effective for providing axial flexibility along the longitudinal axis of the marker and lateral flexibility transverse to the longitudinal axis and which flexibilities are effective to permit the marker to be responsive to changes of shape of the organ, tumor or tumor bed and to follow movements of the organ, tumor, or tumor bed after insertion and after at least one of treatment, natural growth or stresses from the soft tissue while implanted in a patient, the wire of the non-radioactive helical coil marker having a cross section, pitch, helix outer diameter and helix inner diameter which is effective for permitting imaging of the markers with imaging modalities selected from the group consisting of x-ray, radiography, CT scan, ultrasonography, and fluoroscopy; and
    forming one or more images of the one or more markers under one or more of the imaging modalities.

17. The method of claim 16 wherein the ratio of the length of the coil to the outer diameter of the coil is from 10 to 250.

18. A method for observing changes in shape of an organ, tumor or tumor bed of a patient, the method comprising:
    inserting one or more non-radioactive helical coil markers into the soft tissue of the organ, tumor or tumor bed, the one or more helical coil markers being substantially linear just after the insertion, the helical coil markers having a proximal end, a distal end and continuous length, the one or more non-radioactive helical coil markers configured to be held by the soft tissue and being visible under at least one imaging modality and configured to respond to changes in shape of the soft tissue, the one or more non-radioactive helical coil markers in the form of a helical coil with a longitudinal axis, the helical coil having a length, an outer diameter of from about 25 µm to about 2500 µm, a ratio of coil length to coil diameter of 10 or more and a wire diameter of from about 10 µm to about 2500 µm when the wire has a circular cross section or a wire rectangular cross section of from about 10 to about 500 µm, and a ratio of wire cross section width to helical pitch of about 1:1.2±about 0.2, the coil length, wire diameter, ratio of coil length to coil diameter and wire cross section effective for providing axial flexibility along the longitudinal axis of the marker and lateral flexibility transverse to the longitudinal axis and which flexibilities are effective to permit the marker to be responsive to changes of shape of the organ, tumor or tumor bed and to follow movements of the organ, tumor, or tumor bed while implanted in a patient, the wire of the non-radioactive helical coil marker having a cross section, pitch, helix outer diameter and helix inner diameter which is effective for permitting imaging of the markers with imaging modalities selected from the group consisting of x-ray, radiography, CT scan, ultrasonography, and fluoroscopy; and
    forming one or more images of the one or more markers under one or more of the imaging modalities.

19. A marker configured to be imaged when positioned into soft tissue of an organ, tumor or tumor bed within a mammalian body, the marker comprising a non-radioactive helical coil having a length, diameter, a proximal end, a distal end configured for insertion into soft tissue of the organ, tumor or tumor bed and held by the soft tissue inside the body, the marker being visible under at least one imaging modality selected from the group consisting of x-ray, radiography, CT scan, ultrasonography, and fluoroscopy, wherein the marker is a single flexible wire in the form of the helical coil which is configured to be transmitted through a needle and inserted into the soft tissue therefrom and is substantially linear after insertion, the helical coil having an outer diameter of from about 25 µm to about 2500 µm, a ratio of coil length to coil diameter of 10 or more and a wire diameter of from about 10 µm to about 2500 µm when the wire has a circular cross section or a wire rectangular cross section of from about 10 to about 500 µm, and a ratio of wire cross section width to helical pitch of about 1:1.2±about 0.2, the coil length, wire diameter, ratio of coil length to coil diameter and wire cross section effective for providing flexibility along the longitudinal axis of the coil and flexibility transverse to the longitudinal axis which flexibilities are effective to permit the marker to be responsive to changes of shape of the organ, tumor or tumor bed and to follow movements of the organ, tumor, or tumor bed after insertion as a substantially linear coil and after at least one of treatment, natural growth or stresses from the soft tissue after implantation into the soft tissue.

20. The method according to claim 18 wherein the wire of the non-radioactive helical coil marker having a cross section, pitch, helix outer diameter and helix inner diameter which is effective for permitting imaging of the markers with imaging modalities selected from the group consisting of x-ray, radiography, CT scan, ultrasonography, and fluoroscopy.

21. The marker according to claim 19 wherein the helical coil comprises sections of different pitch.

22. The marker according to claim 19 wherein at least portions of the marker are made of a radiopaque material.

23. The marker according to claim 19 wherein the marker comprises biocompatible gold suitable for permanent implantation.

24. The marker of claim 19 wherein the ratio of the length of the coil to an outer diameter of the coil is from 10 to 250.

25. The marker of claim 19 wherein the marker comprises a material selected from the group consisting of rhodium, platinum, iridium, tantalum, titanium, silver, gold, nickel, alloys of these metals, and stainless steel.

* * * * *